US010551354B2

(12) United States Patent
Rautenberg

(10) Patent No.: US 10,551,354 B2
(45) Date of Patent: Feb. 4, 2020

(54) METHOD FOR THE DETERMINING OF PROPERTIES OF A MEDIUM AND DEVICE FOR THE DETERMINING OF PROPERTIES OF A MEDIUM

(71) Applicant: SENSACTION AG, Coburg (DE)

(72) Inventor: Jens Rautenberg, Coburg (DE)

(73) Assignee: SENSACTION AG, Coburg (DE)

(*) Notice: Subject to any disclaimer, the term of this patent is extended or adjusted under 35 U.S.C. 154(b) by 0 days.

(21) Appl. No.: 16/072,135

(22) PCT Filed: Jan. 24, 2017

(86) PCT No.: PCT/EP2017/051448
§ 371 (c)(1),
(2) Date: Jul. 23, 2018

(87) PCT Pub. No.: WO2017/125614
PCT Pub. Date: Jul. 27, 2017

(65) Prior Publication Data
US 2019/0033265 A1    Jan. 31, 2019

(30) Foreign Application Priority Data
Jan. 24, 2016  (DE) .................. 10 2016 200 948

(51) Int. Cl.
*G01F 1/66* (2006.01)
*G01N 29/22* (2006.01)
(Continued)

(52) U.S. Cl.
CPC ........... *G01N 29/222* (2013.01); *G01F 1/662* (2013.01); *G01N 29/022* (2013.01);
(Continued)

(58) Field of Classification Search
CPC .................................. G01F 1/66; G01N 29/22
See application file for complete search history.

(56) References Cited

U.S. PATENT DOCUMENTS

| 4,300,401 | A | 11/1981 | Pedersen |
| 4,735,097 | A | 4/1988 | Lynnworth |

(Continued)

FOREIGN PATENT DOCUMENTS

| DE | 19503714 A1 | 8/1996 |
| DE | 10 2009 048 646 A1 | 3/2011 |

(Continued)

OTHER PUBLICATIONS

EP Office Action in application No. 17 705 026.7 dated Aug. 6, 2019.

(Continued)

*Primary Examiner* — Jewel V Dowtin
(74) *Attorney, Agent, or Firm* — Maschoff Brennan

(57) ABSTRACT

It is provide a method for determining at least one of physical, chemical and biological properties of a medium with the aid of at least two transmitter-receiver pairs and on the basis of at least one first and one second acoustic wave. The first acoustic wave has propagated at least in part between a first transmitter-receiver pair through the medium and the second acoustic wave has propagated at least in part between a second transmitter-receiver pair through the medium, wherein the medium adjoins an inner lateral surface of an elongate conduction element that is arched transversely to its direction of longitudinal extent.

14 Claims, 6 Drawing Sheets

(51) Int. Cl.
*G01N 29/02* (2006.01)
*G01N 29/24* (2006.01)

(52) U.S. Cl.
CPC . *G01N 29/2462* (2013.01); *G01N 2291/0423* (2013.01); *G01N 2291/0428* (2013.01)

(56) References Cited

U.S. PATENT DOCUMENTS

| | | |
|---|---|---|
| 4,838,127 A | 6/1989 | Herremans et al. |
| 6,378,377 B2 | 4/2002 | Matuseski et al. |
| 6,513,365 B1 | 2/2003 | Bruetting et al. |
| 7,943,388 B2 * | 5/2011 | Baetzold ............... C07C 311/51 436/164 |
| 8,234,934 B2 | 8/2012 | Dietz et al. |
| 9,335,259 B2 * | 5/2016 | Gliere ..................... G01N 21/03 |
| 9,581,572 B2 | 2/2017 | Koenig et al. |
| 2015/0260561 A1 | 9/2015 | Twerdowski et al. |
| 2017/0030871 A1 * | 2/2017 | Lobkis ................... G01H 11/00 |

FOREIGN PATENT DOCUMENTS

| | | |
|---|---|---|
| DE | 10 2011 119 673 A1 | 4/2013 |
| DE | 102012019217 A1 | 4/2014 |
| DE | 10 2014 106 706 A1 | 12/2014 |
| EP | 2072972 A1 | 6/2009 |
| EP | 2343548 A2 | 7/2011 |
| EP | 2386835 A1 | 11/2011 |
| WO | 9857163 A1 | 12/1998 |
| WO | 00/64737 | 11/2000 |
| WO | 2008/034878 A2 | 3/2008 |
| WO | 2015/096901 A1 | 7/2015 |

OTHER PUBLICATIONS

Jackson, G.A., et al., "A three-path ultrasonic flowmeter for small-diameter pipelines," vol. 22, pp. 645-650 (1989).

Jackson, G.A., et al., "A three-path ultrasonic flow meter with fluid velocity profile identification," vol. 22, pp. 635-642 (1991).

* cited by examiner

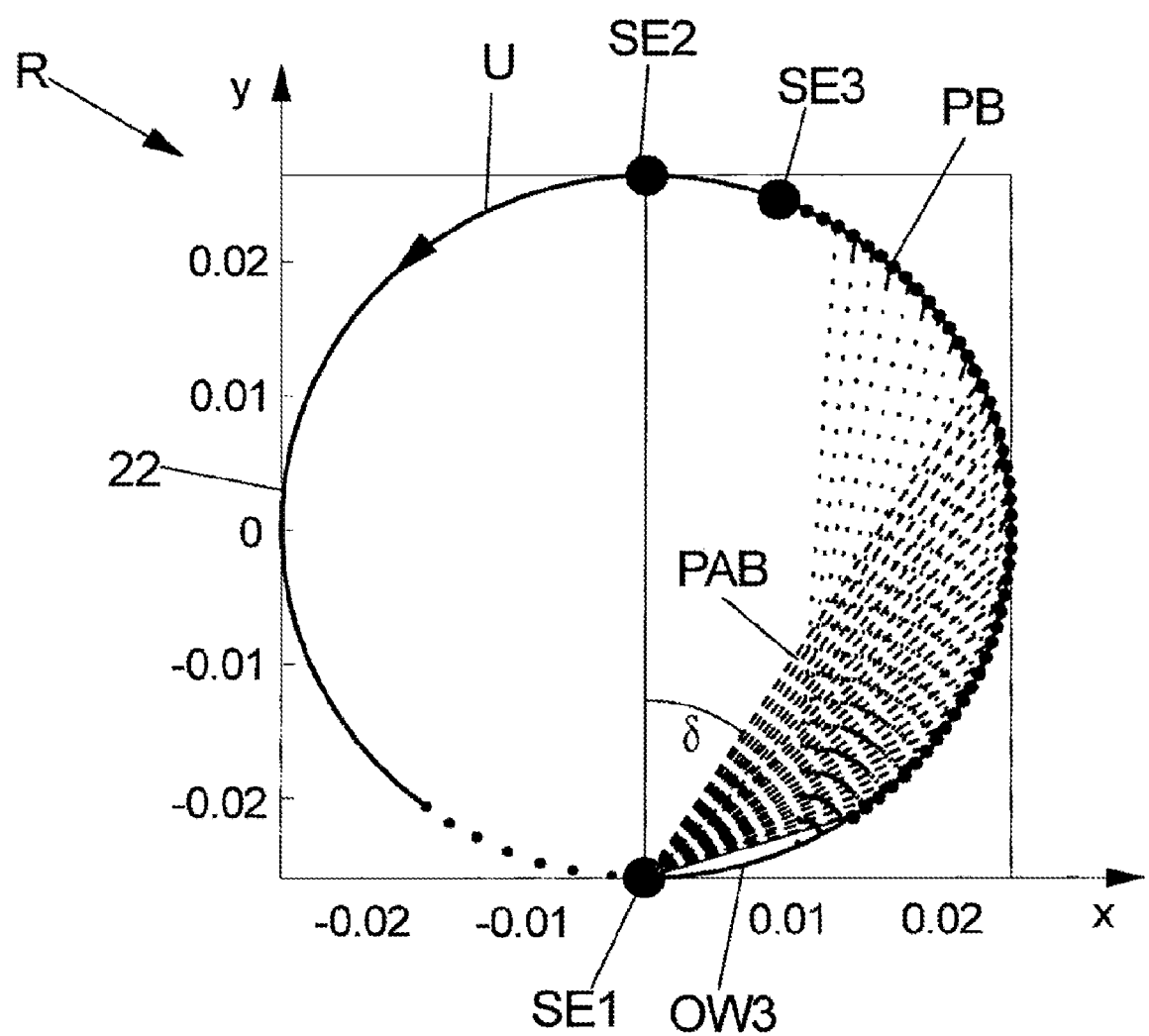

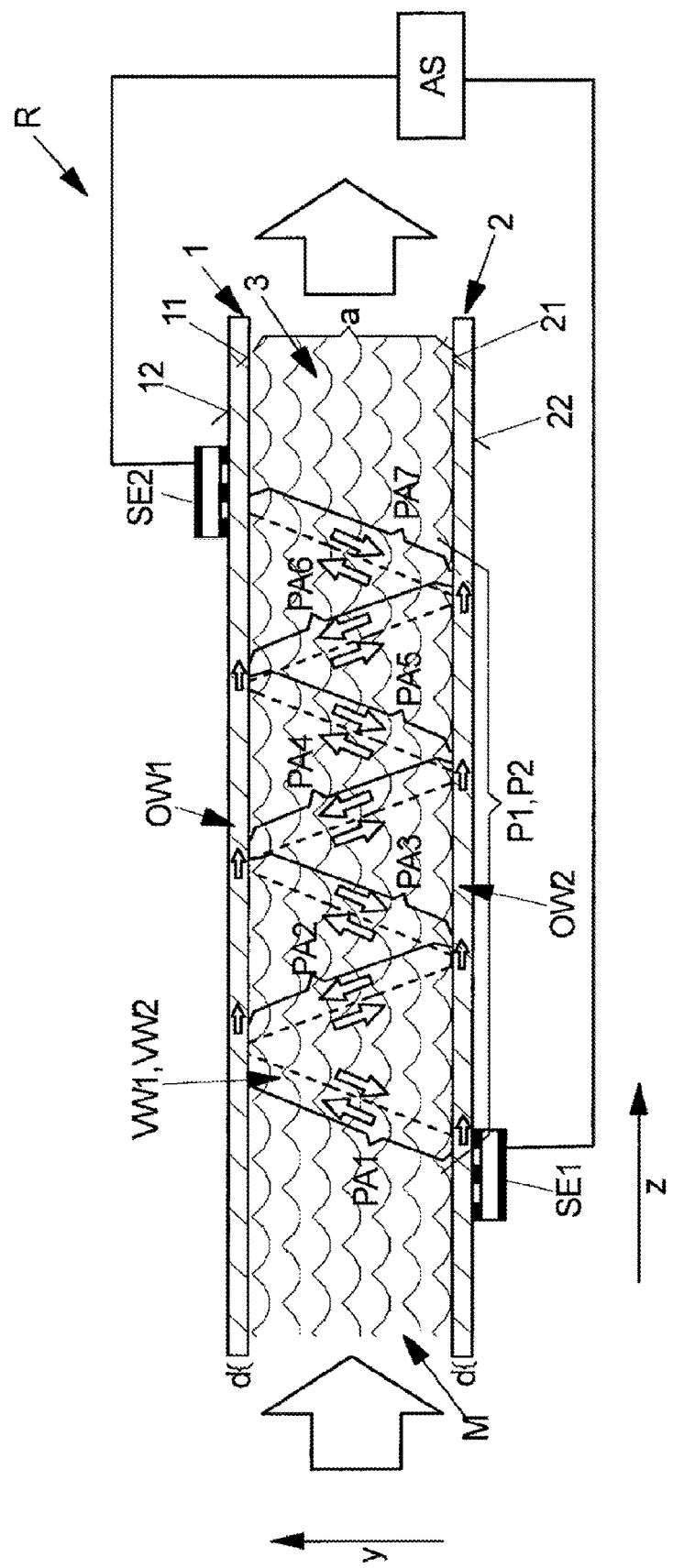

METHOD FOR THE DETERMINING OF PROPERTIES OF A MEDIUM AND DEVICE FOR THE DETERMINING OF PROPERTIES OF A MEDIUM

CROSS-REFERENCE TO A RELATED APPLICATION

This application is a National Phase Patent Application of International Patent Application Number PCT/EP2017/051448, filed on Jan. 24, 2017, which claims priority of German Patent Application 10 2016 200 948.6, filed on Jan. 24, 2016.

BACKGROUND

The present invention relates to a method for determining physical and/or chemical and/or biological properties of a medium and an apparatus for determining physical and/or chemical and/or biological properties of a medium.

The medium whose physical and/or chemical and/or biological properties are to be determined by a generic method is a fluid, preferably a gas, a liquid or a soft material, in particular a highly viscous, dough-like or pasty medium. The acoustic waves used to determine the properties are ultrasonic waves, for example, which are produced by an appropriate transmitter by way of a transmission signal.

In a known method for determining physical, chemical and/or biological properties of the medium, at least two acoustic waves, for example, are produced by a transmission signal, said acoustic waves propagating at least partly through the medium along identical or different propagation directions before they are each received at a receiver lying in the respective propagation direction. By way of example, in a flowing medium, acoustic waves are produced in a first propagation direction in the flow direction of the medium on the one hand and in a second propagation direction counter to the flow direction of the medium on the other hand. Then, a time-of-flight difference can be established from the reception signals generated at the respective receivers and this can be used to deduce the (mean) flow speed of the medium, for example. If, as an alternative or in addition thereto, absolute times of flight of an acoustic wave from a transmitter to a receiver are still established with the aid of the reception signals, it is possible to draw further conclusions about physical, chemical and/or biological properties of the medium, such as the density, temperature or composition thereof, for example.

WO 2008/034878 A2 has disclosed an apparatus in which acoustic surface waves are produced, said surface waves coupling volume acoustic waves into the respective medium in a waveguide. By repeatedly output coupling surface waves at the sites at which the volume acoustic wave strikes a wall surrounding the medium, acoustic surface waves are received at a receiver in turn, the times of flight and time-of-flight differences of said surface waves being characteristic for the medium and the physical, chemical and/or biological properties thereof.

Consequently, in an apparatus described in WO 2008/034878 A2 and in the method implemented therewith, the processing of the reception signals, produced at the respective receivers, for a received acoustic wave—an acoustic surface wave in this case—plays a decisive role. Thus, establishing a time-of-flight difference or an absolute time of flight from the reception signals produced at the receivers is by no means trivial and, in certain circumstances, connected to significant computational outlay. Very different methods for signal processing are used, depending on the information to be extracted from the reception signals. By way of example, the use of modulated transmission signals to be able to deduce the properties of the medium in a more reliable fashion on the basis of the obtained reception signals is known.

Otherwise, there are many (integrated or clamp-on) ultrasonic methods for measuring the flow in pipes. Clamp-on systems are attached to the pipe from the outside and therefore do not change the flow cross section. The acoustic waves always pass centrally through the pipe, which captures the entire flow profile but, as a rule, does not allow a flow profile correction. Consequently, highly accurate flow measurements are only possible in the case of known media and a simultaneous temperature and/or speed of sound measurement. Conventional multi-beam methods, such as those that emerge from DE 195 03 714 A1, EP 2 072 972 A1, EP 2 386 835 A1 or U.S. Pat. No. 4,300,401 A, for example, are able to capture the flow profile in more detail but, as a rule, do not operate without influencing the flow profile since transmitter and/or receiver are introduced into the pipe wall for the purposes of placing the sound paths.

SUMMARY

It is therefore an object of the invention to provide a method, improved in this respect, and an apparatus, improved in this respect, for determining physical, chemical and/or biological properties of a medium.

This object is achieved both by a method with features as described herein and by an apparatus with features as described herein.

In particular, a method is proposed according to the invention for determining physical, chemical and/or biological properties of the meeting with the aid of at least two transmitter-receiver pairs and on the basis of at least one first and one second acoustic wave. Here, the first acoustic wave should have propagated at least in part between a first transmitter-receiver pair through the medium and the second acoustic wave should have propagated at least in part between a second transmitter-receiver pair through the medium, wherein the medium adjoins an inner lateral surface of an elongate conduction element that is arched transversely to its direction of longitudinal extent and wherein a. surface waves are excited at a lateral surface of the conduction element by means of a transmitter of each transmitter-receiver pair, b. surface waves that at least partly arise from a first or second acoustic wave, which was excited by acoustic surface waves propagating at the lateral surface, which propagated in the adjoining medium and which partly coupled back into the lateral surface of the conduction element again as a surface wave, are received by means of a receiver of each transmitter-receiver pair, c. physical, chemical and/or biological properties of the medium are determined by means of the surface waves that were received at the different receivers of the first and second transmitter-receiver pairs, d. surface waves are excited at the lateral surface of the conduction element by a transmitter of the first transmitter-receiver pair, the main propagation direction of said surface waves extending parallel to a direction of longitudinal extent of the conduction element, and e. surface waves are excited at the lateral surface of the conduction element by a transmitter of the second transmitter-receiver pair, the main propagation direction of said surface waves being set to be at a defined angle α in relation to the direction of longitudinal extent of the pipe, where 0°<α<90°.

In this way, surface waves propagate in a helix-type manner at the lateral surface of the conduction element from the transmitter of the second transmitter-receiver pair to the second receiver.

Physical, chemical and/or biological properties, the flow speed of the medium, for example, can be determined by establishing properties of the propagation of different wave trains between transmitter and receiver by means of the signals produced at the receiver upon reception of the wave trains. Here, provision then is made in one configuration for the angle α to be set in such a way that the acoustic waves, usually volume acoustic waves, which are to be coupled into the medium by means of the excited surface waves, always extended an angle σ>30° in relation to the direction of longitudinal extent of the conduction element and to a central axis of the conduction element.

Following the work of Jackson ("*A three-path ultrasonic flow meter with fluid velocity profile identification*", in Meas. Sci. Technol. 2, p. 635-643, 1991), this allows a flow profile correction. According to Jackson, three defined paths in a pipe cross section suffice to be able to establish a symmetric flow profile with sufficient accuracy and use the latter for a flow profile correction of the flow measurement. Attached FIG. 1 from his work shows the required correction factor K for different angles ψ (corresponding to the angle σ explained above) in different axially symmetric flow profiles (ibid, p. 637). Here, a curve A elucidates a correction factor K, plotted against the angle ψ, for a parabolic flow profile, the curve B plots this for a flat flow profile and curves C, D and E plot this for power functions with n=5, 6.5 and 10. Accordingly, in addition to passing sound through centrally, which is used for measuring the speed of sound, density, temperature and concentration according to the prior art, it is necessary to realize two further angles, one of which is significantly greater than 30° in relation to the central axis. In the embodiment variant addressed, this is realized by the surface waves of the second transmitter-receiver pair that, according to the invention, extend obliquely in the medium.

Consequently, the conduction element can be a pipe, for example, which defines an interior that is filled with the medium. However, this can also be a pipe segment, an (open) conduit or a bent plate, which, merely as a part of a sensor device for determining physical, chemical and/or biological properties of the medium, is immersed into an interior, within the pipe, for example, filled with the medium.

The angle α can be set to between 50° and 60°, for example, in particular set at an angle α in the range from 51° to 56°, for a sound speed of the excited surface wave in the range from 600 m/s to 2000 m/s. The the angle α is set to between 37° and 45° in one embodiment variant, in particular set at an angle α in the range from 38° to 44°, if a sound speed of the excited surface wave in the range from 600 m/s to 1150 m/s is predetermined. By setting the angle ranges specified above by means of the transmitter, it is possible to configure the transmitter and receiver to be comparatively compact since the emerging sound paths between transmitter and receiver are comparatively narrow and this allows a good compromise to be obtained, in particular between a sufficiently long dwell time of the sound packet in the flow medium (as result of which a large measurement effect emerges) and an angle σ greater than 30°. Here, the angle ranges specified above are obtained by appropriate positioning and design of the transmitter. Here, the appropriate positioning of the transmitter can arise, for example, from calculations or by trials.

In a development, additionally, at least one further, third transmitter-receiver pair is provided, the latter exciting surface waves by a transmitter of the third transmitter-receiver pair, the propagation direction of said surface waves being set to be a defined angle γ in relation to the direction of longitudinal extent of the conduction element, where 0°<γ<90°. By way of example, this allows an even more precise flow measurement in a particularly simple manner.

For a sound speed of the excited surface waves in the range of 600 m/s to 1150 m/s, the angle for a third transmitter-receiver pair then is likewise set to between 37° and 45°, for example, in particular to an angle γ in the range from 38° to 44°.

For a significant improvement in the measurement accuracy, the settings of the transmitter and the position of the receiver of a third transmitter-receiver pair—like in the case of the second transmitter-receiver pair—are undertaken and matched to one another in such a way that a receiver of a third transmitter-receiver pair then can receive surface waves which, proceeding from the transmitter of this transmitter-receiver pair, have only propagated along the outer lateral surface in a helical manner.

As already addressed above, the proposed method can be used to carry out a comparatively very exact flow measurement by means of the surface waves received at the different receivers of the first and second transmitter-receiver pairs and to determine the flow speed of the medium through the conduction element. A flow profile can be established and a flow profile correction can be undertaken when determining the flow speed of the medium on the basis of the surface waves received at the different receivers of the first and second transmitter-receiver pairs.

According to a second aspect of the invention, an apparatus for determining physical, chemical and/or biological properties of a medium is proposed, comprising an acoustic waveguide having an elongate conduction element that is arched transversely to its direction of longitudinal extent, a medium to be characterized being able to adjoin the latter, at least two transmitter-receiver pairs, wherein a. surface waves are excitable at a lateral surface of the conduction element by means of a transmitter of each transmitter-receiver pair, and b. surface waves that at least partly arise from acoustic waves, which are excited by acoustic surface waves propagating at the lateral surface, which propagate in the medium and which partly couple back into the lateral surface of the conduction element again as a surface wave, are receivable by means of a receiver of each transmitter-receiver pair, and an electronic evaluation device coupled to the different receivers of the first and second transmitter-receiver pairs, by means of which physical, chemical and/or biological properties of the medium are determinable surface waves received at different receivers of the first and second transmitter-receiver pairs.

Here, provision is additionally made for a transmitter of the first transmitter-receiver pair to be configured and arranged at an outer lateral surface of the conduction element so as to excite surface waves whose main propagation direction extends parallel to the direction of longitudinal extent of the conduction element, and a transmitter of the second transmitter-receiver pair to be configured and arranged at an outer lateral surface of the conduction element so as to excite surface waves whose main propagation direction is set to be at a defined angle α in relation to the direction of longitudinal extent of the conduction element, where 0°<α<90°.

For a sound speed of the excited surface waves in the region from 600 m/s to 2000 m/s, the transmitter of the second transmitter-receiver pair once again can be configured and arranged on the outer lateral surface of the conduction element in such a way that the angle α is set to between 50° and 60°, in particular to an angle α in the range from 51° to 56°. The angle α can be set to between 37° and 45° by the transmitter, in particular set at an angle α in the range from 38° to 44°, for a sound speed of the excited surface wave in the range from 600 m/s to 1150 m/s.

As already explained above with reference to the proposed method, the apparatus can additionally comprise at least one further, third transmitter-receiver pair, in which a transmitter of the third transmitter-receiver pair is configured and arranged at an outer lateral surface of the conduction element so as to excite surface waves whose propagation direction is set to be a defined angle γ in relation to the direction of longitudinal extent of the conduction element, where 0°<γ<90°.

For a sound speed of the surface waves, to be excited by the transmitter of the third transmitter-receiver pair, in the region from 600 m/s to 1150 m/s, the transmitter of the third transmitter-receiver pair likewise can be configured and arranged on the outer lateral surface of the conduction element in such a way that the angle γ is set to between 37° and 45°, in particular to an angle γ in the range from 38° to 44°.

In principle, a transmitter and/or a receiver can be formed by a transducer, in particular an interdigital transducer or a wedge transducer.

Here, in particular, the proposed method is implementable by means of the proposed apparatus such that advantages and features of embodiment variants of the method, explained both above and below, also apply to embodiment variants of the apparatus, and vice versa.

BRIEF DESCRIPTION OF THE DRAWINGS

The attached figures elucidate possible exemplary embodiments of the proposed solution in an exemplary manner.

FIGS. 3A-3B show an embodiment variant of a measurement apparatus for presenting the positions of transmitter and receiver of the transmitter-receiver pairs while elucidating comparatively narrow helical sound path bands proceeding from a (common) transmitter.

FIG. 4 shows a measurement apparatus known from the prior art.

DETAILED DESCRIPTION

Figure 1:
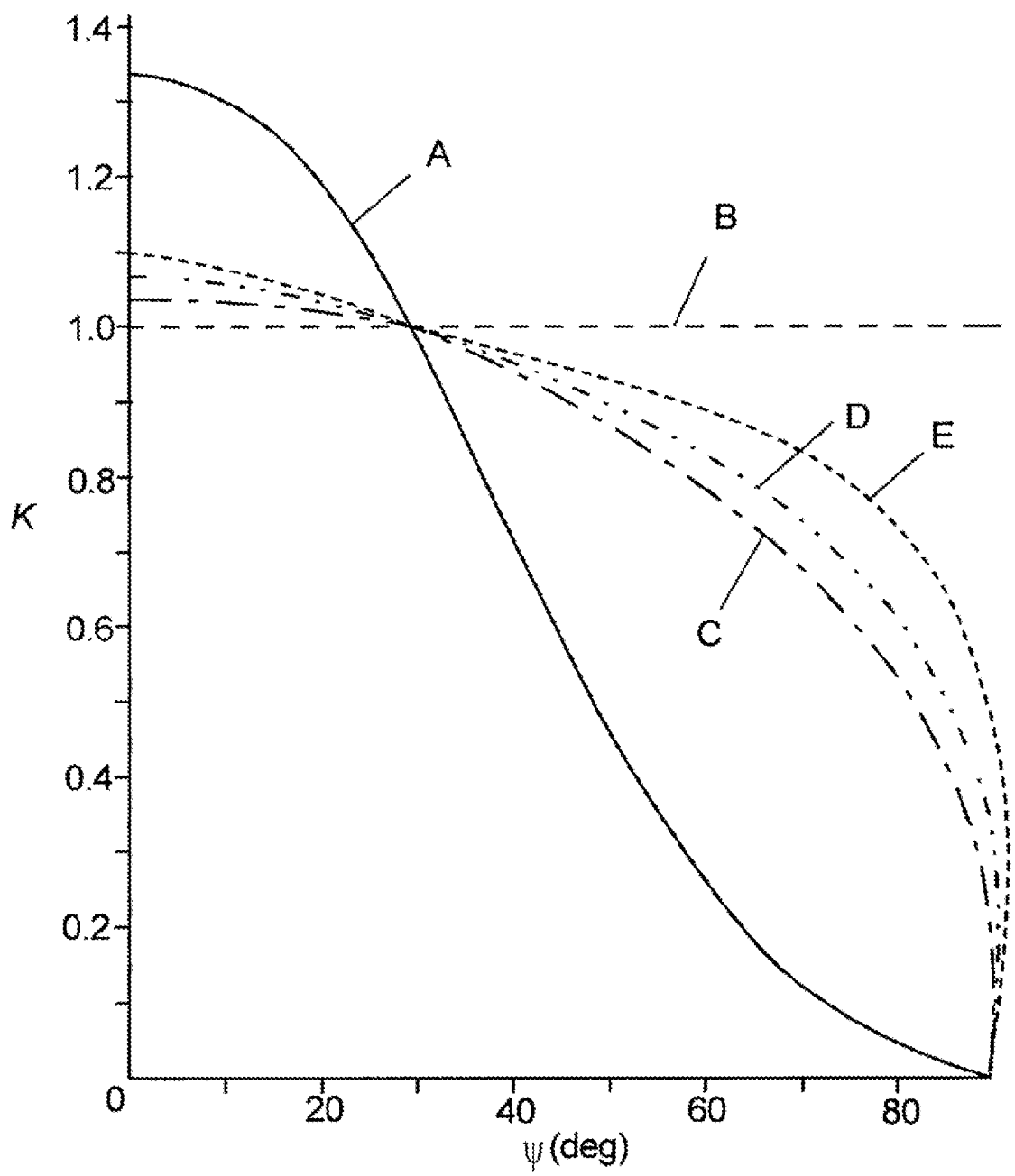
FIG. 1 shows a diagram for elucidating a correction factor K for different angles ψ in the case of different axially symmetric flow profiles.

The cut view of FIG. 4 shows, in part, a (measurement) apparatus already known per se, which is embodied and provided for determining physical, chemical and/or biological properties of a medium M, in particular for determining or measuring a flow speed of the flowing medium M. An acoustic waveguide with two substrates 1, 2 as conduction elements of the waveguide is part of the measurement apparatus, with the medium M flowing through the waveguide. The substrates 1, 2, which lie opposite one another and the (inner) surfaces 11, 21 of which that face one another extend parallel to one another along the main direction of extent of the waveguide, are produced from a non-piezoelectric material. Here, the substrates are opposite portions of a continuously cylindrical, preferably circularly cylindrical pipe sheath of the pipe R.

These substrates 1, 2 lie opposite one another at a distance a and, in the present case, they are edged by two wall portions of the pipe R that lie opposite one another at this distance a, said wall portions forming a (channel-shaped) interior 3 of the pipe acting as a waveguide or of a pipe piece. The medium M to be measured, which is schematically illustrated by wavy lines, is filled into the interior 3, wherein the medium M can flow through the interior 3. In principle, the flow direction of the liquid or flowable medium M through the interior 3 is as desired. In the present case, there is a flow from an inlet opening to an outlet opening along the direction of extent z of the waveguide and parallel to the inner surfaces 11, 21. In FIG. 4, the flow direction is indicated by arrows at the output opening and inlet opening.

A first transmitter-receiver unit SE1 and a second transmitter-receiver unit SE2 are assigned to the two (first and second) substrates 1 and 2 of the waveguide of the apparatus, said transmitter-receiver units together forming a (first) transmitter-receiver pair. Here, each transmitter-receiver unit SE1, SE2 is operable in at least two different modes of operation as, firstly, a transmitter and, secondly, a receiver in order to excite and receive surface waves. Consequently, for example, the first transmitter-receiver unit SE1 of the second substrate 2 can be (initially) operated as a transmitter while the second transmitter-receiver unit SE2 of the substrate 1 is operated as a receiver.

The transmitter and receiver units SE1, SE2 are arranged in each case at an outer surface 22 or 12 of the respective substrate 2 or 1 or externally at the lateral surface of the pipe R, which lies opposite an inner surface 21 or 11 that faces the interior 5 with the medium M in each case. The two transmitter-receiver units SE1, SE2 are preferably piezoelectric transducers with interdigital electrodes or full-area piezoelectric transducers with a wedge-shaped delay path. Preferably, a transmitter-receiver unit SE1, SE2 is fastened to the respective substrate 2, 1 by adhesive bonding, such that said units can be assembled in a simple and quick manner. Alternatively, other attachment styles can also be provided.

In the present case, the first transmitter-receiver unit SE1 of FIG. 4 is in the region of the first end of the waveguide while the second transmitter-receiver unit SE2 is arranged in the region of another, second end of the waveguide and the waveguide extends between these two ends along the main direction of extent z in the illustrated cross-sectional view.

By way of a transmitter-receiver unit, e.g. SE1, operating as a transmitter, acoustic surface waves OW2 are produced in the substrate 2 by means of a predetermined, preferably pulse-like transmission signal. Some of the energy of these produced acoustic surface waves OW2 is coupled into the medium M at the interface of the inner surface 21 as a volume acoustic wave VW1. The propagation of the volume acoustic wave VW1 and the propagation direction of the volume acoustic wave VW1 are illustrated schematically here in FIG. 4 by a dashed line and by an arrow next to this dashed line. Two arrows pointing in opposite directions to the dashed lines in each case next indicate that the volume acoustic waves propagate along path portions PA1 to PA7, represented by the dashed lines, in one direction during one mode of operation of the apparatus and in the other direction during another mode of operation of the apparatus.

The two substrates 1, 2, which form the inner surfaces 12, 21, preferably consist of a non-piezoelectric material and have a thickness d, which is defined as the spacing of the inner surfaces 11, 21 (=nominal width of the pipe) of the respectively assigned outer surfaces 12 and 22, respectively. In the present case, the thickness d is less than or equal to the wavelength of the respectively produced acoustic surface waves. As a result of this, acoustic surface waves, which propagate within the substrates 1, 2, can have such wave properties that they propagate both along the inner surfaces 11, 21 and along the outer surfaces 12, 22 of the plate-shaped substrates 1, 2. Consequently, Lamb waves or waves in the transition region between Lamb waves and Rayleigh waves are excited. Depending on the thickness d of the plates of the substrates 1, 2, acoustic surface waves will be present here substantially in the form of Lamb waves (d less than the wavelength of the acoustic surface waves) or in the form of waves from the transition region between Lamb waves and Rayleigh waves (d equal to the wavelength of the acoustic surface waves). In any case, the acoustic surface waves in the present case propagate along both surfaces 11, 12 and 21, 22 of the substrates 1 and 2.

As elucidated in FIG. 4, the acoustic surface waves OW2, for example, therefore extend along the direction of extent z of the second substrate 2 and, in particular, along the inner surface 21 of this substrate 2, propagating from the transmitter-receiver unit SE1 operating as a transmitter. Some of the acoustic wave energy of the acoustic surface waves OW2 propagating along the inner surface 21 of the substrate 2 is coupled into the medium M situated within the interior 3, and so the volume acoustic waves VW1 are produced within the medium M. Here, a propagation direction of these input-coupled volume acoustic waves VW1 is inclined relative to the normal of the flat surface 21 by a characteristic angle $\Delta$, which is not plotted here.

The volume acoustical waves VW1 in each case propagate along a path P1 in the medium M. This path can be subdivided into various portions PA1, PA2, PA3, PA4, PA5, PA6, PA7 illustrated by dashed lines. Each of these path portions extends between the one (second) substrate 2 and the other (first) substrate 1. As soon as the volume acoustic wave VW1 has reached an interaction site at the inner surface 11 of the opposite substrate 1, some of its energy is coupled into the substrate 1, and so acoustic surface waves OW1, for example in the form of Lamb waves or surface waves in the transition region of Lamb waves and Rayleigh waves, are produced herein, said surface waves propagating along the substrate 1.

Further, there is an interaction of the acoustic wave with a corresponding substrate 1, 2 at each instant at which the volume acoustic wave VW1 reaches the inner surface 11 or 21 of one of the substrates 1, 2. Here, as a rule, there is an energy exchange of acoustic energy between the substrate 1, 2, in particular the surface wave OW1, OW2 of the respective substrate 1, 2, and the volume acoustic wave VW1. The volume acoustic wave VW1 is at least partly reflected and it changes its direction of propagation in the process. If the interaction consists of energy being coupled from the volume acoustic wave VW1 into the relevant surface wave OW1, the amplitude of the surface wave OW1 is increased by this input coupling and the amplitude of the volume acoustic wave VW1 reduces. However, alternatively, energy of the surface wave OW1 can be coupled into the volume acoustic wave VW1 depending on the properties of the substrate and of the medium M, and depending on the wave.

Consequently, a plurality of interaction sites are defined by the interaction of the volume acoustic wave VW1 with the substrates 1, 2 along the path P1 thereof. At these interaction sites, the volume acoustic wave VW1 in each case interacts with a substrate 1, 2 and the surface waves OW1, OW2 occurring in the substrate 1, 2. Thus, overall, (first) wave trains comprising volume acoustic waves VW1 propagate on a substantially zigzag-shaped propagation path P1 in the medium between the first transmitter-receiver unit SE1 and the second transmitter-receiver unit SE2 along the main direction of extent of the waveguide. On account of the interaction of the volume acoustic wave VW1 with the first substrate 1, lying opposite the second substrate 2, at the inner surface 11 of said first substrate, there is an excitation of surface waves OW1 that can propagate on the substrate 1 and can finally be received at the transmitter-receiver unit SE2 operating as a receiver. Surface waves OW1 propagate without amplification between the interaction sites of the second substrate 2, i.e., the sites at which the volume acoustic waves VW1 interact with the second substrate 2, but they may (possibly) experience a further amplification at the subsequent interaction sites. By measuring the wave trains arriving at the receiver E, in particular the surface waves OW1 which were excited by the interaction with the volume acoustic wave VW1, it is possible to ascertain the time of flight of wave trains between the first and second transmitter-receiver units SE1, SE2.

Thus, the sound speed within the medium M can be deduced from the acoustic surface waves OW1 (or groups of surface waves OW1), which successively arrive at the transmitter-receiver unit SE2 operating as a receiver, in particular if the time of flight of the wave trains between the transmitter-receiver units SE1, SE2 is determined. Using a further transmitter-receiver unit on the substrate 2, arranged at quite some distance from SE1, it is possible to obtain additional amplitude information. The ratio of the amplitudes measured at SE2 and at the further transmitter-receiver unit can be used to deduce the substance density of the medium. Since the measured times of flight and amplitudes of the acoustic surface waves OW1 input coupled by the volume acoustic wave VW1 at the respective interaction sites can be influenced by the properties of the medium M, this allows physical, chemical and/or biological properties of the medium M to be measured to be determined by an electronic evaluation device AS, to which the signals of a transmitter and receiver unit SE2 are forwarded. Here, the reception signal is produced in each case from an acoustic wave received at the transmitter-receiver unit SE2 or SE1, said acoustic wave having at least partly propagated through the medium M from the other transmitter-receiver unit SE1, SE2 to this transmitter-receiver unit SE2, SE1 as a volume acoustic wave VW1 (or VW2).

It should be noted that a receiver or a transmitter-receiver unit SE2 operated in a receiver mode usually only receives surface waves OW1, with these surface waves OW1 originating from the volume acoustic wave VW1 striking the first substrate 1. The ascertained time differences between the reception of one or more surface wave(s) is accordingly also used as a basis for determining the flow speed, as will still be explained in more detail below.

To this end, the apparatus of FIG. 4 can be operated by way of a multiplexer in two different modes of operation; i.e., the second transmitter-receiver unit SE2 previously operated in a receiver mode is operated in a transmitter mode and the first transmitter-receiver unit SE1 previously operated in the transmitter mode is operated in the receiver mode. Here, an acoustic surface wave OW1 is also excited in the first substrate 1 by the second transmitter-receiver unit SE2 operated in the transmitter mode. At least some of the energy of this acoustic surface wave OW1 is converted, as previously, into energy of an acoustic volume acoustic wave VW2 that propagates in the medium M, said acoustic volume acoustic wave now propagating on a propagation path P2 from the second transmitter-receiver unit SE2 to the first transmitter-receiver unit SE1 through the medium M. The surface wave OW1 of the second acoustic wave, excited by the second transmitter-receiver unit SE2, consequently emanates from this transmitter-receiver unit SE2 such that the volume acoustic wave VW2 excited thereby extends substantially opposite to the previous volume acoustic wave VW1 and extends in a zigzag shape through the medium M in the direction of the first transmitter-receiver unit SE1.

By way of switching between transmitter and receiver mode of the transmitter-receiver units SE1, SE2, the propagation direction of the volume acoustic waves VW1, VW2 is consequently reversed within the medium M along the main direction of propagation of the waveguide. Hence, what emerges is that, depending on the mode of operation, (first or second) wave trains or first or second acoustic waves propagate between the two transmitter-receiver units SE1 and SE2 in such a way that, on the one hand, they have path portions PA1 to PA7 extending in the medium, along which they have a propagation velocity with a propagation velocity component in the direction of the flow of the medium M (first wave trains) and propagate in such a way that, on the other hand, they have path portions PA7 to PA1 extending in the medium, along which they have a propagation velocity with a propagation velocity component in the opposite direction to the flow of the medium M (second wave trains). Consequently, the times of flight for the surface waves received at the first transmitter-receiver unit SE1 of the second wave train deviate from the times of flight for surface waves of the first wave train received at the second transmitter-receiver unit SE2 on account of the flow of the medium M. By measuring the (absolute) times of flight of the two wave trains and/or by establishing a difference in the times of the flight of the mutually opposing wave trains, it is consequently possible, in principle, to determine the flow speed of the medium M. Further, information about the sound speed, the density or the concentration of substances in the medium M can be derived by way of the propagation of the wave trains along the waveguide.

However, deducing a time-of-flight difference or even the absolute time of flight of an acoustic wave between the transmitter-receiver units SE1, SE2 on the basis of the received signals for incoming acoustic waves (reception signals) is by no means trivial and may require an enormous computational outlay in certain circumstances. Incidentally, this also applies to other measurement apparatuses in which physical, chemical and/or biological properties of the medium are determined with the aid of the acoustic waves.

Now, this is the starting point for a method according to the invention, which provides a further transmitter-receiver pair, in which surface waves are excited by a transmitter of the second transmitter-receiver pair, the (main) direction of propagation of which is set to a defined angle $\alpha$ in relation to the direction of longitudinal extent of the pipe, where $0° < \alpha < 90°$. In this way, the surface waves excited obliquely to the central axis of the pipe under the angle $\alpha$ propagate in a helical manner at the lateral surface of the pipe toward the second receiver.

A sound packet that is excited in a preferred direction or mean propagation direction of extent (angle $\alpha$, proceeding from the pipe axis projected onto the pipe wall) on the lateral surface 22 of the pipe R propagates helically on this lateral surface 22 with the phase speed $c_{Ph}$ of a Lamb wave on the pipe wall (illustrated in black/with dots in FIGS. 2A, 2B, 3A and 3B). Proceeding from the initial point (x(t=0)=0, y(t=0)=−R, z(t=0)=0), the following curve (x(t),y(t),z(t)) of possible primary sound paths in the pipe wall is obtained, where r describes the radius of the pipe:

$$x(t)=r^*\sin(c_u^*t/R)$$

$$y(t)=-r^*\cos(c_u^*t/R)$$

$$z(t)=c_z^*t$$

Here, $c_u$ and $c_z$ are the phase sound speeds of the Lamb wave projected in the circumferential direction or pipe axis, where $c_u=c_{Ph}^*\sin(\alpha)$ and $c_{Ph}=\cos(\alpha)$, i.e., $\tan(\alpha)=c_u/c_z$.

As already illustrated with reference to FIG. 4, the Lamb waves, during the propagation thereof, decouple at least some sound into the enclosed medium M or fluid, wherein there is a straight-lined propagation of the sound (proceeding from the zero point "0", respectively illustrated in the right image part in FIGS. 2A and 3A and respectively illustrated in the left image part in FIGS. 2B and 3B) before the acoustic wave is coupled into the pipe R again. These re-coupling sound components continue their propagation, at least in part, in the lateral surface 22 as a helix with the same grade (reciprocity) and form a secondary sound path. The arrangement with sound reception should now be conditioned such that it, as it were, covers the directly emitted sound (i.e., the firstly formulated helix, primary wave) and the secondary helix in a predetermined range of the sound speed of the fluid. Here, the angle $\alpha$ is preset in such a way that the sound path in the medium over the whole value range of the presently possible sound speed always adopts an angle of greater than 30° with respect to the central axis of the pipe R (denoted by angles β1 and β2 in FIG. 2A) and bridges a sufficiently long path in the longitudinal direction z of the pipe R (=> measurement effect).

Figure 2A:
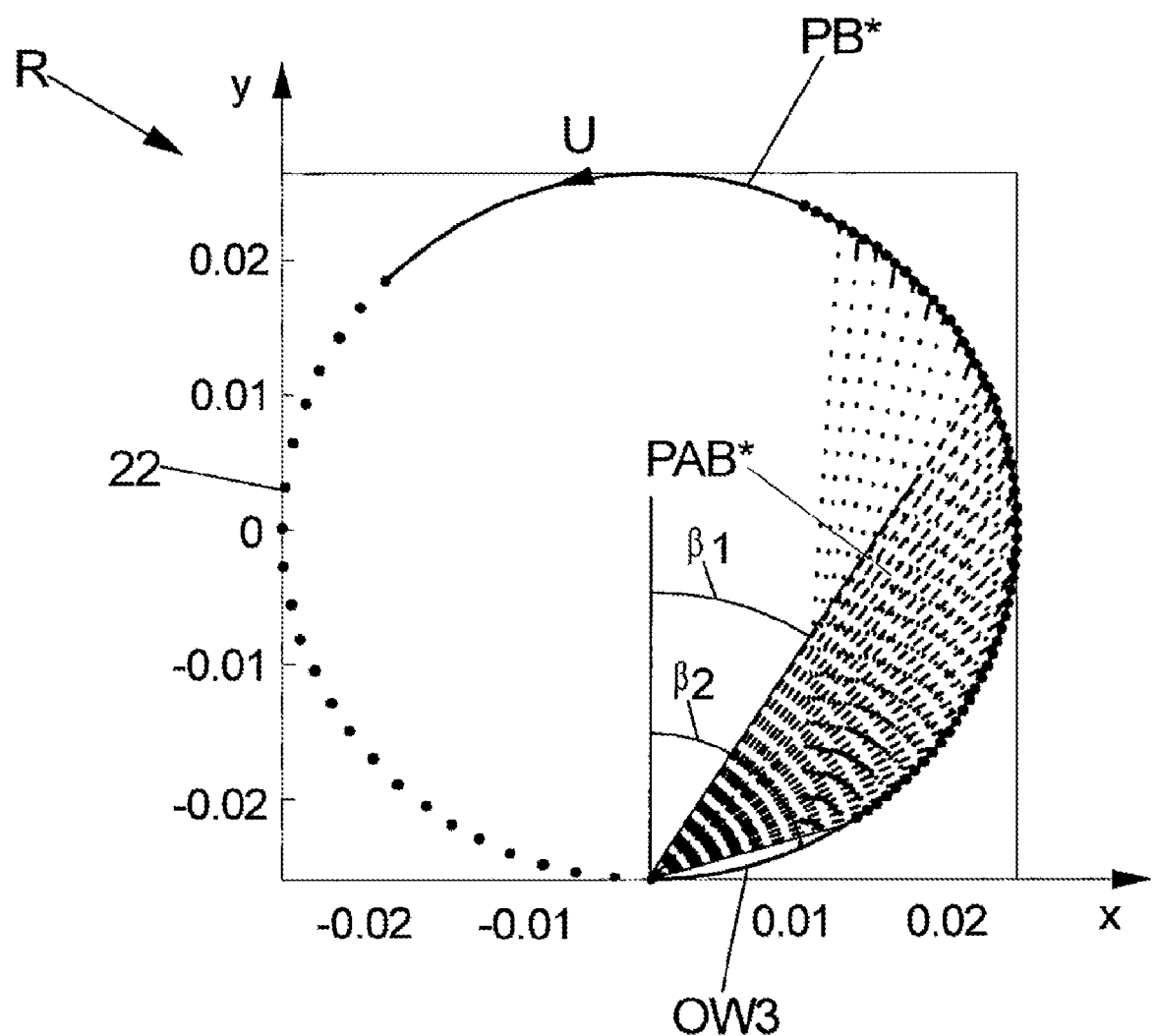
FIGS. 2A-2B show an embodiment variant of the measurement apparatus while elucidating a comparatively broad helical sound path band proceeding from a transmitter of a transmitter-receiver pair of the measurement apparatus.
Figure 2B:
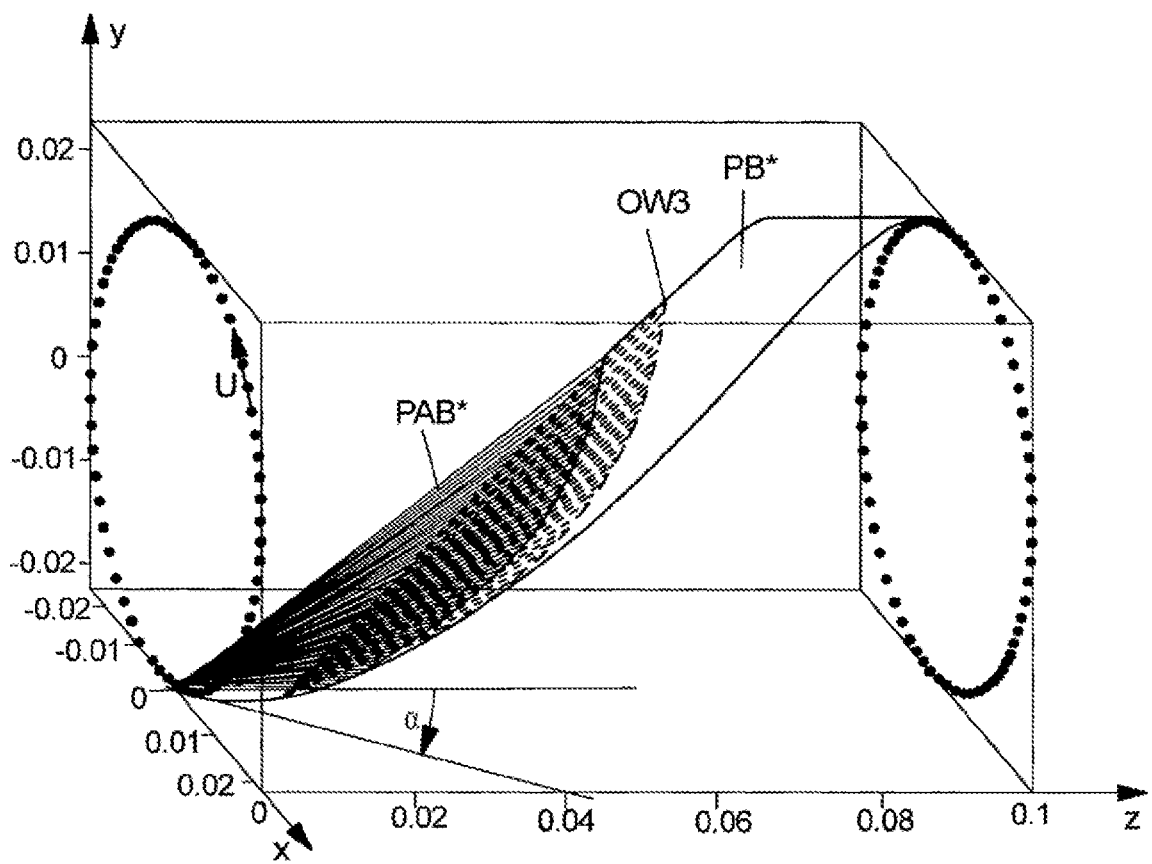

An apparatus in which the angle $\alpha$ is set to 40° is elucidated on the basis of FIGS. 2A and 2B. The sound paths within the medium M that are possible over an admissible sound speed range of 2000 m/s to 600 m/s, which are elucidated by way of the bundle of sound path portions PAB*, are sufficiently tilted (between angles β1 and β2 at sound speeds of 2000 and 600 m/s) and also in the fluid for long enough (>20 mm in the case of DN50, for example). However, the primary and secondary helix of surface waves OW3 propagating between a transmitter and a receiver of a second transmitter-receiver pair at the lateral surface 22 of the pipe R still form a comparatively broad path on the pipe wall 22 (illustrated as part of the path bundle PB*). This makes a uniform detection of both components using only one transducer more difficult.

By way of example, a placement of transmitter-receiver pairs SE1, SE2 and SE1, SE3 at a pipe R, in which, for a large range of the sound speeds (600 m/s-2000 m/s), work is carried out with at least one additional transmitter/receiver or only exactly one additional transmitter-receiver pair and an angle $\alpha$ in the range from 51° to 56°, can be provided on the basis of the solution according to the invention as a possible compromise between a sufficiently long dwell time of the sound packet in the flowing medium M (larger measurement effect resulting therefrom) and an angle σ greater than 30° in relation to the center axis of the pipe R and a tightly edged sound path in the pipe wall 22 such that it is possible to place minimally small transducers for transmitting and receiving the sound packets on the pipe wall 22 (corresponds to 11 in FIG. 4). This allows a flow-profile-corrected flow measurement to be carried out. Consequently, for an effective flow profile compensation, the path portions of the volume acoustic waves that are coupled into the medium M and that propagate through the medium M, which are illustrated as a beam PAB for the different sound speeds in FIGS. 3A and 3B, cover an angle range for the angle σ from approximately 30° to 61°.

Figure 3B:
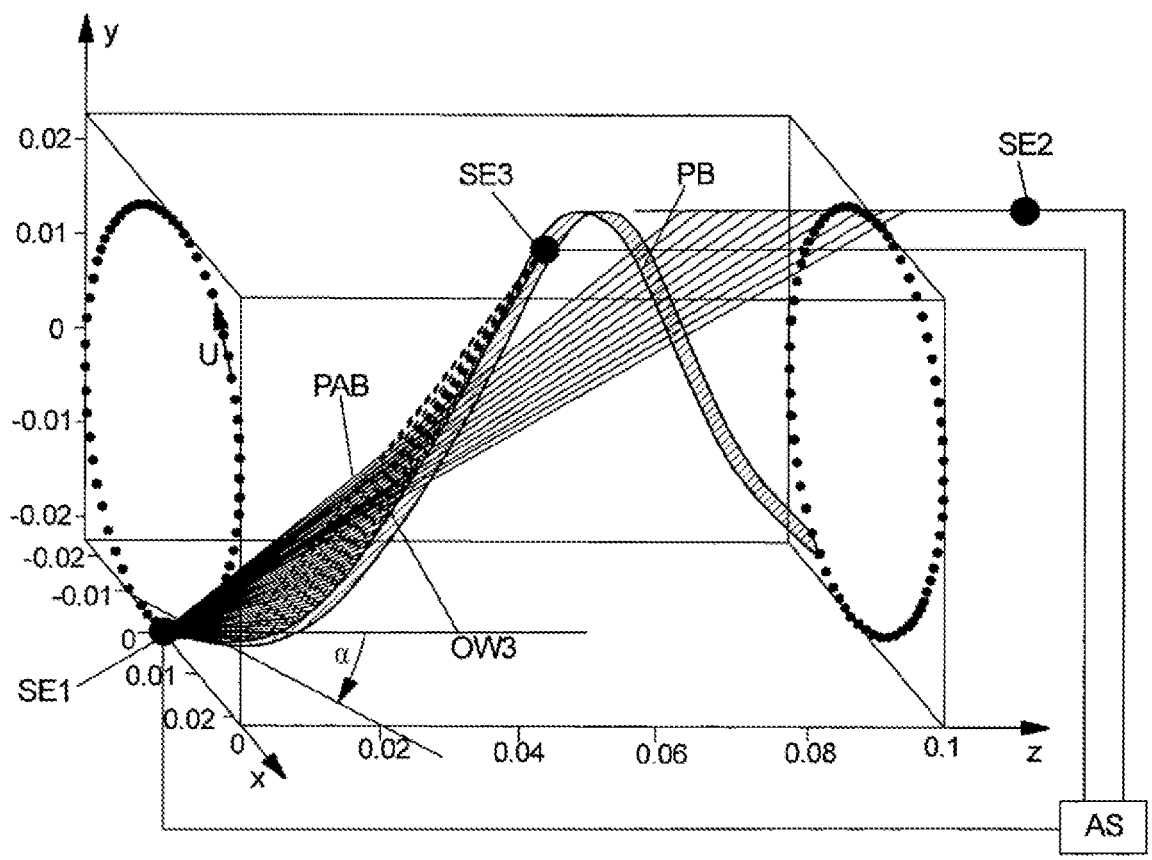

An exemplary configuration of the measurement apparatus (in this case DN50, but arbitrarily scalable in size) is elucidated by FIGS. 3A and 3B, which further illustrate the position of the second transmitter-receiver pair SE1, SE3. A first transmitter-receiver pair SE1, SE2 is equally arranged at the lateral surface of the pipe R, corresponding to FIG. 4. The position of the transmitter-receiver units SE1 and SE3, embodied as transducers in an exemplary manner, is marked in FIGS. 3A and 3B. They are aligned with the main emission direction in the direction of the plotted helix of the path bundle PB (which corresponds to the aforementioned value range for the angle α).

In principle, a transmitter can be assigned to a plurality of transmitter-receiver pairs, in particular both the first and second transmitter-receiver pair, or each transmitter-receiver pair can have a dedicated transmitter that is positioned differently to, and also spatially separated from, a transmitter of another transmitter-receiver pair. A transmitter-receiver unit operated as a transmitter and/or receiver is usually embodied as an acoustic transducer, for example in the form of an interdigital transducer or a wedge transducer.

In one variant, a transmitter SE1 of the second transmitter-receiver pair SE1, SE3 is configured and arranged on the outer lateral surface 22 of the pipe R for the purposes of exciting surface waves OW3, the propagation direction of which are set to a defined angle α with respect to the direction of longitudinal extent z of the pipe R in the range from 38° to 44° for a sound speed range from approximately 600 m/s to 1150 m/s.

Alternatively or in addition thereto, at least one additional, third transmitter-receiver pair still is provided in one variant. For the purposes of increasing the measurement effect for a sound speed range from approximately 600 m/s to 1150 m/s, it is preferable in that case to set the main emission direction of the transmitter in such a way that surface waves OW3 are excited at the lateral surface 22 of the pipe R, the main direction of propagation of which is set to a defined angle γ with respect to the direction of longitudinal extent z of the pipe R in the range from 38° to 44°. By way of example, this allows an even more precise flow measurement in a particularly simple manner.

A measurement apparatus configured according to the invention, in particular on the basis of an embodiment variant of FIG. 2A, 2B or 3A, 3B, can also be used for recognizing asymmetric flow profiles and the automatic correction thereof when determining the flow speed of the medium M through the pipe R. Here, it is then possible to provide further transmitter-receiver pairs in addition to the first and second and optionally in addition to a third transmitter-receiver pair as well, in particular transmitter-receiver pairs in which surface waves OW3 are excited at the lateral surface 22 of the pipe R by a transmitter, the main direction of propagation of said surface waves being set to a defined angle >0° in relation to the direction of longitudinal extent z of the pipe R.

Moreover, it is obvious that the presented apparatuses and the methods implemented herewith not only can determine a (mean) flow speed of a flow medium M and can consequently render a flow measurement performable but can also—in an alternative or complementary manner—carry out a measurement of concentration, thickness, distance, temperature and/or fill level, as is already largely known in comparable apparatuses that operate using acoustic waves, in particular ultrasonic waves. The same applies to determining time-dependent curves of a current amplitude or current phase of the received acoustic waves and values for density and viscosity of the medium M derived therefrom.

LIST OF REFERENCE SIGNS 1 (First) substrate
11 Inner surface/inner lateral surface
12 Outer surface
2 (Second) substrate
21 Inner surface
22 Outer surface/outer lateral surface
3 Interior
AS Electronic evaluation device
a Distance
d Thickness
M Medium
OW1, OW2, OW3 Surface wave
P1, P2 Path
PA1-PA7 Path portion
PB, PB* Path bundle
PAB, PAB* Bundle of possible path portions
SE1, SE2, SE3 Transmitter-receiver unit/transducer
R Pipe
VW1, VW2 Volume acoustic wave
α, β1, β2, σ Angle
u Circumferential direction

The invention claimed is:

1. A method for determining at least one of physical, chemical and biological properties of a medium with the aid of at least two transmitter-receiver pairs and on the basis of at least one first and one second acoustic wave, wherein the first acoustic wave has propagated at least in part between a first transmitter-receiver pair through the medium and the second acoustic wave has propagated at least in part between a second transmitter-receiver pair through the medium, wherein the medium adjoins an inner lateral surface of an elongate conduction element that is arched transversely to its direction of longitudinal extent and wherein:

surface waves are excited at a lateral surface of the conduction element by means of a transmitter of each transmitter-receiver pair, surface waves that at least partly arise from a first or second acoustic wave, which was excited by acoustic surface waves propagating at the lateral surface, which propagated in the medium and which partly coupled back into the lateral surface of the conduction element again as a surface wave, are received by means of a receiver of each transmitter-receiver pair, at least one of physical, chemical and biological properties of the medium are determined by means of the surface waves that were received at the different receivers of the first and second transmitter-receiver pairs, surface waves are excited at the lateral surface of the conduction element by a transmitter of the first transmitter-receiver pair, the main propagation direction of said surface waves extending parallel to the direction of longitudinal extent of the conduction element, and surface waves are excited at the lateral surface of the conduction element by a transmitter of the second transmitter-receiver pair, the main propagation direction of said surface waves being set to be at a defined angle α in relation to the direction of longitudinal extent of the conduction element, where 0°<α<90°.

2. The method as claimed in claim 1, wherein the angle α is set to between 50° and 60°, in particular set at an angle α in the range from 51° to 56°, for a sound speed of the excited surface wave in the range from 600 m/s to 2000 m/s.

3. The method as claimed in claim 1, wherein the angle α is set to between 37° and 45°, in particular set at an angle α in the range from 38° to 44°, for a sound speed of the excited surface wave in the range from 600 m/s to 1150 m/s.

4. The method as claimed in claim 1, wherein, additionally, at least one further, third transmitter-receiver pair is provided, in which surface waves are excited by a transmitter of the third transmitter-receiver pair, the propagation direction of said surface waves being set to be a defined angle γ in relation to the direction of longitudinal extent of the conduction element, where 0°<γ<90°.

5. The method as claimed in claim 4, wherein the angle γ is set to between 37° and 45°, in particular set at an angle γ in the range from 38° to 44°, for a sound speed of the excited surface wave in the range from 600 m/s to 1150 m/s.

6. The method as claimed in claim 1, wherein a receiver of a second or third transmitter-receiver pair receives surface waves that, proceeding from a transmitter of this transmitter-receive pair, have only propagated along an outer lateral surface in a helical manner.

7. The method as claimed in claim 1, wherein, by means of surface waves that are captured at the different receivers of the first and second transmitter-receiver pairs, a flow measurement is carried out and a flow speed of the medium through the conduction element is determined.

8. The method as claimed in claim 7, wherein, on the basis of surface waves that are captured at the different receivers of the first and second transmitter-receiver pairs, a flow profile is established and a flow-profile correction is undertaken when determining the flow speed of the medium.

9. An apparatus for determining at least one of physical, chemical and biological properties of a medium, comprising:

an acoustic waveguide having an elongate conduction element that is arched transversely to its direction of longitudinal extent, a medium to be characterized being able to adjoin the latter, at least two transmitter-receiver pairs, wherein:

surface waves are excitable at a lateral surface of the conduction element by means of a transmitter of each transmitter-receiver pair, and surface waves that at least partly arise from acoustic waves, which are excited by acoustic surface waves propagating at the lateral surface, which propagate in the medium and which partly couple back into the lateral surface of the conduction element again as a surface wave, are receivable by means of a receiver of each transmitter-receiver pair, and an electronic evaluation device coupled to the different receivers of the first and second transmitter-receiver pairs, by means of which at least one of physical, chemical and biological properties of the medium are determinable surface waves received at different receivers of the first and second transmitter-receiver pairs, wherein:

a transmitter of the first transmitter-receiver pair is configured and arranged at an outer lateral surface of the conduction element so as to excite surface waves whose propagation direction extends parallel to the direction of longitudinal extent of the conduction element, and a transmitter of the second transmitter-receiver pair is configured and arranged at the outer lateral surface of the conduction element so as to excite surface waves whose propagation direction is set to be at a defined angle α in relation to the direction of longitudinal extent of the conduction element, where 0°<α<90°.

10. The apparatus as claimed in claim 9, wherein the angle α is set to between 50° and 60°, in particular set at an angle α in the range from 51° to 56°, for a sound speed of the excited surface wave in the range from 600 m/s to 2000 m/s.

11. The apparatus as claimed in claim 9, wherein the angle α is set to between 37° and 45°, in particular set at an angle α in the range from 38° to 44°, for a sound speed of the excited surface wave in the range from 600 m/s to 1150 m/s.

12. The apparatus as claimed in claim 9, wherein, additionally, at least one further, third transmitter-receiver pair is provided, in which a transmitter of the third transmitter-receiver pair is configured and arranged at the outer lateral surface of the conduction element so as to excite surface waves whose propagation direction is set to be a defined angle γ in relation to the direction of longitudinal extent of the conduction element, where 0°<γ<90°.

13. The apparatus as claimed in claim 12, wherein the angle γ is set to between 37° and 45°, in particular set at an angle γ in the range from 38° to 44°, for a sound speed of the excited surface wave in the range from 600 m/s to 1150 m/s.

14. The apparatus as claimed in claim 9, wherein a transmitter and/or a receiver are formed by a transducer, in particular an interdigital transducer or a wedge transducer.

* * * * *